US010682549B2

(12) United States Patent
Edelhaeusser et al.

(10) Patent No.: US 10,682,549 B2
(45) Date of Patent: Jun. 16, 2020

(54) DEVICE AND METHOD FOR AUTOMATICALLY EVALUATING A PROGRESSION OF A TRAINING EXERCISE

(71) Applicant: Fraunhofer-Gesellschaft zur Foerderung der angewandten Forschung e.V., Munich (DE)

(72) Inventors: Thorsten Edelhaeusser, Neuenkirchen a. Brand (DE); Nicolas Witt, Nuremberg (DE); Matthias Voelker, Hessdorf (DE); David Voll, Roethenbach a. d. Pegnitz (DE); Stephan Otto, Heroldsberg (DE); Ingmar Bretz, Regenstauf (DE); Norbert Franke, Erlangen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 160 days.

(21) Appl. No.: 15/035,216

(22) PCT Filed: Nov. 7, 2014

(86) PCT No.: PCT/EP2014/074041
§ 371 (c)(1),
(2) Date: May 6, 2016

(87) PCT Pub. No.: WO2015/067753
PCT Pub. Date: May 14, 2015

(65) Prior Publication Data
US 2016/0271448 A1 Sep. 22, 2016

(51) Int. Cl.
*A63F 9/24* (2006.01)
*A63B 24/00* (2006.01)
(Continued)

(52) U.S. Cl.
CPC ........ *A63B 24/0062* (2013.01); *A61B 5/1113* (2013.01); *A63B 24/0021* (2013.01);
(Continued)

(58) Field of Classification Search
CPC .......... A63B 24/0062; A63B 2220/833; A63B 2024/0025
See application file for complete search history.

(56) References Cited

U.S. PATENT DOCUMENTS

| 6,837,827 B1 | 1/2005 | Lee et al. | |
| 2003/0087220 A1* | 5/2003 | Bessette | A63B 24/0062 434/247 |
| 2007/0300157 A1* | 12/2007 | Clausi | G06F 3/04883 715/719 |

(Continued)

FOREIGN PATENT DOCUMENTS

| CN | 102512804 A | 6/2012 |
| DE | 202013100964 U1 | 5/2013 |

(Continued)

*Primary Examiner* — Steve Rowland
(74) *Attorney, Agent, or Firm* — Yong Beom Hwang; 2SPL Patent Attorneys (57) ABSTRACT

Embodiments relate to a method for automatically evaluating a progression of a training exercise, including providing a plurality of location information for at least one movable object participating in the training exercise and providing at least one predetermined exercise target. The plurality of location information is compared to the exercise target and a progression of the training exercise is evaluated based on the result of the comparison.

23 Claims, 3 Drawing Sheets

(51) Int. Cl.
  *G09B 19/00* (2006.01)
  *G06F 19/00* (2018.01)
  *A61B 5/11* (2006.01)
  *G09B 5/02* (2006.01)

(52) U.S. Cl.
  CPC ........... *G06F 19/3481* (2013.01); *G09B 5/02* (2013.01); *G09B 19/0038* (2013.01); *A61B 2503/10* (2013.01); *A61B 2505/09* (2013.01); *A63B 2024/0028* (2013.01)

(56) References Cited

U.S. PATENT DOCUMENTS

| | | | |
|---|---|---|---|
| 2008/0258921 | A1 | 10/2008 | Woo et al. |
| 2009/2100780 | | 8/2009 | Crowley |
| 2010/0041498 | A1 | 2/2010 | Adams |
| 2010/0160014 | A1* | 6/2010 | Galasso ............ A63B 24/0021 463/6 |
| 2010/0184563 | A1* | 7/2010 | Molyneux ........... A43B 1/0054 482/1 |
| 2011/0169959 | A1 | 7/2011 | DeAngelis et al. |
| 2012/0053828 | A1 | 3/2012 | Haneishi et al. |
| 2012/0116550 | A1* | 5/2012 | Hoffman ............ A63B 24/0084 700/91 |
| 2012/0191229 | A1 | 7/2012 | Woo et al. |
| 2014/0094232 | A1* | 4/2014 | Framel .................... H04W 4/21 463/6 |
| 2014/0222177 | A1* | 8/2014 | Thurman ........... G09B 19/0038 700/92 |
| 2015/0131845 | A1* | 5/2015 | Forouhar ........... G06K 9/00724 382/100 |

FOREIGN PATENT DOCUMENTS

| | | |
|---|---|---|
| EP | 2189191 | 5/2010 |
| RU | 2107328 C1 | 3/1998 |
| WO | 0187426 A2 | 11/2001 |
| WO | 2005048199 A1 | 5/2005 |
| WO | 2013041124 A1 | 3/2013 |
| WO | 2013064172 | 5/2013 |
| WO | 2013064174 | 5/2013 |
| WO | 2013126655 | 8/2013 |

* cited by examiner

DEVICE AND METHOD FOR AUTOMATICALLY EVALUATING A PROGRESSION OF A TRAINING EXERCISE

Embodiments of the present invention relate to a device and a method for automatically evaluating a progression of a training exercise, particularly in sports.

Evaluating a training exercise in sports may be helpful to arrive at a direct and objective comparison between the performances of individual participants in the training exercise. Furthermore, the evaluation of the progression of the training exercise may help to recognize that it makes sense to change the training exercise itself. The video analysis is often used for this purpose, i.e., the objects involved in the training exercise, such as athletes or play equipment, e.g. balls, or similar are filmed during the progression of the exercise using video recording equipment. The progression of the exercise and/or the training is evaluated, for example, by the coach by sifting through the video material. This is extremely time-consuming and also involves a high latency between actually holding the exercise and receiving the results. Further, in the evaluation, there is always a subjective aspect which results from the evaluation of the scenes by the coach and/or the video camera's angle of view. This may lead to it being very difficult to perform the direct comparison between two athletes or objects involved in the training exercise in an objective way.

Therefore, there is a demand for improving the evaluation of a progression of a training exercise.

Embodiments of the present invention facilitate this by a method and/or a device and a system according to any one of the independent claims.

An embodiment of a method for automatically evaluating a progression of a training exercise comprises providing a plurality of location information for at least one movable object participating in the training exercise. Further, at least one predetermined exercise target is provided and the plurality of location information for the movable object is compared to the predetermined exercise target. The progression of the training exercise is evaluated based on the result of this comparison. Providing the plurality of location information for a movable object in connection with providing and/or previously defining at least one predetermined exercise target makes it possible to evaluate the progression of a training exercise in an automated and objective manner. For example, in this way a qualitative statement concerning a success may also be derived.

Further, the evaluation may be carried out in a timely manner. According to some embodiments, the evaluation may be carried out in real time or at a very low latency so that it may possibly be decided that the training exercise needs to be repeated, something that is hardly possible in a conventional manner. For example, if necessary, the effort made for the time-shifted, repeated set-up of the training exercise may be saved. However, due to the objective analysis, timely spaced identical training exercises may also be evaluated using the same benchmarks, something that enables a comparison of objects participating in the training exercises over long periods as well. Movable objects participating in the training exercise may, for example, be athletes whose position was recorded and/or determined within a predetermined exercise area using a position tracking system while carrying out the training exercise. Generally speaking, a movable object participating in the training exercise may, however, also be any other object such as a sports item, e.g., a ball, a javelin thrown, a discus thrown or a pole of a pole vaulter and/or the bar which a high jumper needs to clear.

According to some embodiments, providing the at least one predetermined exercise target comprises selecting at least one used determination logic for the location information from a plurality of available determination logics. By the possibility of using different determination logics, according to the embodiments of the invention, any questions for any sport or case of application may be answered. Depending on the case of application, selecting a determination logic comprises merely selecting a predefined determination logic, adapting or changing a predefined determination logic and defining a new determination logic, something that may facilitate to address any question.

According to the determination logic used, a tactical parameter or a technical parameter is determined for a sport according to some embodiments. According to these embodiments, for example, training exercises may thus be evaluated which aim at training tactical behavior patterns. The suitable determination logic thus facilitates to answer more complicated questions which may go far beyond information directly correlating to the observed location. However, according to some embodiments, an athletic parameter for at least one person involved in the training exercise may, also, or in addition, be determined using the determination logic used and based on the location information. It is obvious in this context that, according to the embodiments of the invention, several questions may be addressed at the same time, wherefore for example several determination logics to be used may be selected and defined while providing the exercise target.

According to some embodiments, a piece of location information for the object respectively shows a position of the object within a predetermined exercise area. A relative relationship of the position to an exercise area may enable one and the same training exercise to be held at different physical locations if the coordinates in each case are indicated in relation to the exercise area and not in an absolute coordinate system. The coordinate system and/or its illustration as such may be random, for example the positions of the movable and immovable objects involved in the training exercises may be indicated in Cartesian coordinates, in polar coordinates or in geographic coordinates. The number of dimensions is not specified either. Depending on the embodiment, one-, two- or three-dimensional coordinates may be used.

According to some embodiments, the plurality of location information is provided by a position tracking system which senses the position of the movable object within the exercise area at several successive points in time. Such a tracking system supplies, e.g., positions for athletes, training material and/or exercise objects and other delimitations of the exercise area. The positions of the objects may here be acquired in any way, e.g., using a video-based, a radio-based or an acoustic locating and/or position tracking system.

According to some further embodiments, exercise objects and/or stationary training equipment is also taken into account in the evaluation of the success of the training exercise. According to further embodiments, at least one further piece of location information for an exercise object or a time-invariant position within the exercise area is provided for this purpose which corresponds to a predetermined progression of the training exercise. A piece of location information for an exercise object corresponds here, e.g., to an object which cannot move by its own strength. Such objects and/or stationary or immovable training material may for example be cones, poles or positioners as well as lines which indicate and/or delimit pitches or specified movement directions. Therefore, exercise objects in this sense are, for example, real objects which, even though they may basically be movable, e.g., cones or similar, may only be moved by interaction with an athlete or any other movable object. In other words, exercise objects may be such objects of which the possible movement is not a target of the exercise. In this context, exercise objects may hereinafter also be referred to as immovable objects.

According to some embodiments, the piece of location information and/or the position of an immovable object involved in the training exercise is directly specified by a user. For example, this may be done by inputting the associated coordinates. According to some embodiments, this is done using a graphical user interface comprising a graphical illustration of the exercise area and of the objects involved in the training exercise. According to these embodiments, the positioning of the immovable object may take place by moving a graphical representation of the object within the graphical illustration of the exercise area up to its desired position. According to further embodiments, the position of immovable objects within the exercise area may also be sensed and/or provided using a position tracking system. Depending on the special implementation of the position tracking system, this may for example be done by applying additional markings and/or tags on the exercise material and/or the immovable objects. Alternatively, coordinates for objects present within the exercise area, e.g., for lines, goals or similar already present there, may also be sensed.

According to some embodiments, providing the predetermined exercise target also comprises defining parameters which should initially be determined for the movable object based on the location information to evaluate the success of the training exercise. Such parameters may, for example, be the speed of the object, the speed of a direction change of the object, a route covered within a predetermined time unit, a number of direction changes per time unit or similar.

Accordingly, exercise targets provided for automatically evaluating the training exercise may be various criteria, such as the entering of the object into a predetermined sector within the exercise area, e.g., to detect a successful shot on goal and/or a successful dribbling in a sector in front of a goal. According to further embodiments, a predetermined exercise target is, for example, an interaction of the movable object with a further object, reaching of a predetermined speed by the object or a consistency of the provided location information with a predetermined sequence of location information. A predetermined sequence of location information may, for example, define a desired trajectory of a player on the pitch who should follow the same during the training exercise. A comparison of the deviation of the actual movement of the movable object and/or of the player from the specified trajectory may be a benchmark for the successful completion of the training exercise. For example, any overstepping of lines, ball contacts, speeds, paths, running statistics, passes and further results may be identified as well.

Some embodiments of the present invention evaluate the progression of the training exercise online and/or in real-time and display a visual illustration of the evaluation of the progression of the training exercise on a screen. This may comprise a visual illustration of the results of the comparison of the location information with the exercise target, e.g., in absolute figures or in a relative illustration which compares the number of successful comparisons and the number of unsuccessful comparisons.

According to further embodiments, the plurality of location information and the exercise target and, if available, the location information for further immovable objects, which are a part of the training exercise, are stored for later use, e.g., in a database. This may facilitate to create and/or adapt the exercise targets as a follow-up to analyze the training exercise already performed with regard to changed and/or adapted criteria possibly unknown at the time when the exercise was held.

In other word, evaluating the training exercise may take place when the exercise is ongoing and/or is held, or offline.

Some embodiments further comprise a system for evaluating a success of a progression of a training exercise additionally comprising a position tracking system configured to sense location information for at least one movable object participating in the training exercise within an exercise area. The system further comprises an analyzer configured to evaluate the progression of the training exercise based on the aspects described above, and of which the input interface is configured to receive the location information of the position tracking system.

Preferred embodiments are hereinafter explained in more detail with reference to the enclosed Figures.

Various embodiments will now be described more fully with reference to the accompanying drawings in which some embodiments are illustrated. In the Figures, the thicknesses of lines, layers and/or regions may be exaggerated for clarity.

In the following description of the accompanying Figures, which merely show some exemplary embodiments, like reference numbers may refer to like or comparable components. Furthermore, summarizing reference numbers may be used for components and objects which occur several times in an embodiment or in a drawing, but are described jointly with regard to one or several features. Components or objects which are described using like or summarizing reference numbers may be realized in the same way—however, if necessary, also be implemented differently—with regard to individual, several or all features, such as their dimensionings.

Even though embodiments may be modified and amended in various ways, embodiments in the Figures are represented as examples and are described in detail herein. However, it is made clear that it is not intended to limit embodiments to the particular forms disclosed, but on the contrary, embodiments should cover any and all functional and/or structural modifications, equivalents, and alternatives falling within the scope of the invention. Like reference numbers refer to like or similar elements throughout the entire description of the Figures.

It should be noted that, when an element is referred to as being "connected" or "coupled" to another element, it can be directly connected or coupled to the other element or intervening elements may be present. In contrast, when an element is referred to as being "directly connected" or "directly coupled" to another element, no intervening elements are present. Other terms used to describe the relationship between elements should be interpreted in a like fashion (e.g., "between" versus "directly between", "adjacent" versus "directly adjacent", etc.).

The terminology used herein is for the purpose of describing particular embodiments only and is not intended to limit the embodiments. As used herein, the singular forms "a," "an" and "the" are intended to include the plural forms as well, unless the context clearly indicates otherwise. It is further made clear that the terms, e.g., "comprises," "comprising," "includes" and/or "including," as used herein, indicate the presence of stated features, integers, steps, operations, elements and/or components, but do not preclude the presence or addition of one or more further features, integers, steps, operations, elements, components and/or groups thereof.

Unless defined otherwise, any and all terms (including technical and scientific terms) used herein have the same meaning as commonly understood by one of ordinary skill in the art to which embodiments belong. It is further made clear that terms, e.g., those defined in commonly used dictionaries, should be interpreted as having a meaning that is consistent with their meaning in the context of the relevant art and should not be interpreted in an idealized or overly formal sense unless expressly defined herein.

Figure 1:
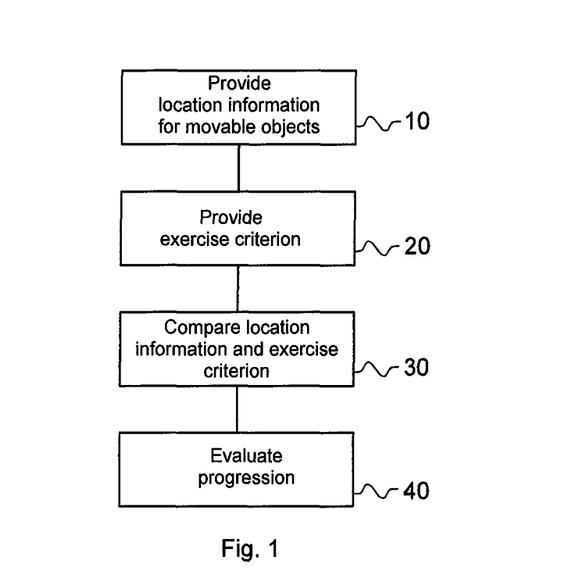
FIG. 1 shows a flow diagram of an embodiment of a method for evaluating a progression of a training exercise.

The method for automatically evaluating a progression of a training exercise comprises providing 10 a plurality of location information for at least one movable object participating in the training exercise and further providing 20 at least one predetermined exercise target. During the analysis, a comparison 30 of the plurality of location information with the exercise target is carried out and/or the location information is analyzed in relation to the exercise target. In this respect, the location information may either be directly compared to an exercise target or, based on the location information, quantities derived therefrom may be determined which are then taken as a basis for a comparison, e.g., a speed, an acceleration, an average rate of direction changes per time unit or similar. Further examples for quantities to be calculated comprise sprint times for a predetermined route or the so-called tapping frequency indicating a number of steps of an athlete which the same is able to perform at one spot per second. For example, a tapping frequency of 15 per second or a sprint time of 10 seconds for a 100 meter sprint could be defined as an exercise target. To determine the tapping frequency, for example, a plurality of sensors may be attached to an athlete each of which supplies several pieces of location information per time unit so that, for example, the orientation of an athlete's limbs may be determined as well. In other words, the plurality of location information for at least one movable object participating in the training exercise may come from several sensors. When evaluating 40 the progression of the training exercise, the evaluation is carried out based on the result of the comparison 30. For example, it might be evaluated as being positive if a single exercise target was achieved or if, in case of multiple repetition of an exercise, the exercise target was achieved by more than a predetermined percentage.

In this respect, the order of these method steps is not fixed, for example, the predetermined exercise target and/or the exercise targets used to evaluate the progression of the training exercise may be provided before the location information is provided or collected. Likewise, one or several exercise targets may be provided and/or defined only after a real exercise has been performed.

Providing the at least one exercise target and/or the typically several exercise targets, by means of which the training exercise is evaluated, may also be referred to as drawing up an exercise template. This may be done in connection with the definition of the material used during the training exercise, amongst other, including a definition of the movable and immovable objects which are used within, and/or are part of, the training exercise. Hence, providing the predetermined exercise targets may comprise the definition of the objects and the definition of the material used as well as a definition of further determination logic, i.e., for example, a selection of parameters to be analyzed such as intermediate times, paths, the number of passes or similar. Further, providing an exercise target may comprise the definition of the purpose of an exercise as well as a definition of an area and/or a predetermined exercise area and the teams involved. To define the teams involved, for example, the positions of individual fellow players of team sports acquired using an automatic position tracking system may be associated with different teams.

In other words, given the high flexibility of the embodiments any determination logic may be used to address almost any question.

According to some embodiments, tactical parameters may here be determined and may be taken as a basis for the evaluation of the success of a training exercise, for example. An example for a tactical parameter is the form of the trajectory covered by a participant in the training exercise. The evaluation of the success may, for example, be done by comparing specified target paths and/or trajectories for particular moves, e.g., in soccer, football, hockey, handball, etc., to the actually determined trajectories. A further requirement for a determination logic might be that one or several participants in the training exercise should not leave a specified zone, or that the duration of stay of a participant in the "marking area" (Deckungss-chatten) of another participant should be evaluated, wherein a shorter duration of stay may be evaluated as being better than a longer one. Examples for further tactical parameters are the distances between exercise material and fellow players and/or between fellow players themselves. For example, an exercise target may be that the distances within a back four should be complied with, wherein a feedback is given if such distances become too large or too small. Further possible parameters are the distance between tracked poles and/or cones, which should be circulated in a narrow slalom or the size of a space covered by a participant or a team as well as the compactness (=surface area) of a team which could be measured, e.g., by a polygon surrounding the team.

According to further embodiments, sport-specific technical parameters may be determined and may be taken as a basis for the evaluation of the success of a training exercise. An example for this would be passes and their characteristics, e.g., the number of passes per time unit, the speed of a pass, the time in ball possession before a pass. If, for example, forcing a fast-paced game is defined as an exercise target, the time passed before the pass should on average lie below a determined threshold value. Further parameters to be determined may, for example, be the number of ball contacts before a pass (direct passes might be an exercise target, i.e., a ball contact) as well as the ratio of successful passes (which arrive at a fellow player) to the unsuccessful passes (which arrive at an opponent or go out). Further examples for a ball sport may relate to the ball contacts, e.g., the number of ball contacts with the right and/or left foot and their comparison with a requirement comprised in the exercise target. Further examples relate to shots on goal and their characteristics, such as the shot speed, the zone in the goal which should be and/or was hit or the goal distance for a final shot. As a generalization for this, specific distances or zones may be specified as specified limits and may be taken as a basis for the evaluation. If a free-kick exercise is evaluated, a desired trajectory for a ball might, for example, be specified as an exercise target, e.g., left/right past the wall or below the wall.

According to further embodiments, athletic parameters may be determined, such as the route covered by a participant of the training exercise. During rehab training, a training exercise might then, for example, be evaluated as being successful if a specified route was covered.

As a further athletic parameter, the speed may for example be determined. According to the determination logic, it might then for example be determined as to how often a maximum speed was achieved, as to how close a participant came to the required speed and as to whether or not a participant exceeded or fell short of a predetermined speed. As a further athletic parameter, the step length and the step frequency might be determined for example. According to the determination logic, it might then be determined as to whether or not the target, to use short quick steps, was achieved. According to the determination logic, the running intensity might also be determined to evaluate as to whether or not the exercise target sprint, running fast, running medium-fast, running slowly, walking or standing was achieved, or as to whether or not a specified sequence of running intensities was complied with in a more complex training exercise.

According to some embodiments, defining the exercise template may also comprise providing at least one piece of location information for a time-invariant position within the exercise area which does not correspond to any physical object. This piece of location information may be referred to as corresponding to a virtual material. An example for this is a virtual line or a virtual point within the exercise area if the same is important for a wanted and/or predetermined progression of the training exercise. For example, such a virtual line may indicate when a player has moved out of a permissible exercise area, something that may, for example, result in an unsuccessful abandonment of the exercise and/or might be classified in such a way. Likewise, such a line might serve as a start and/or end criterion, e.g., for time measurements.

Figure 2:
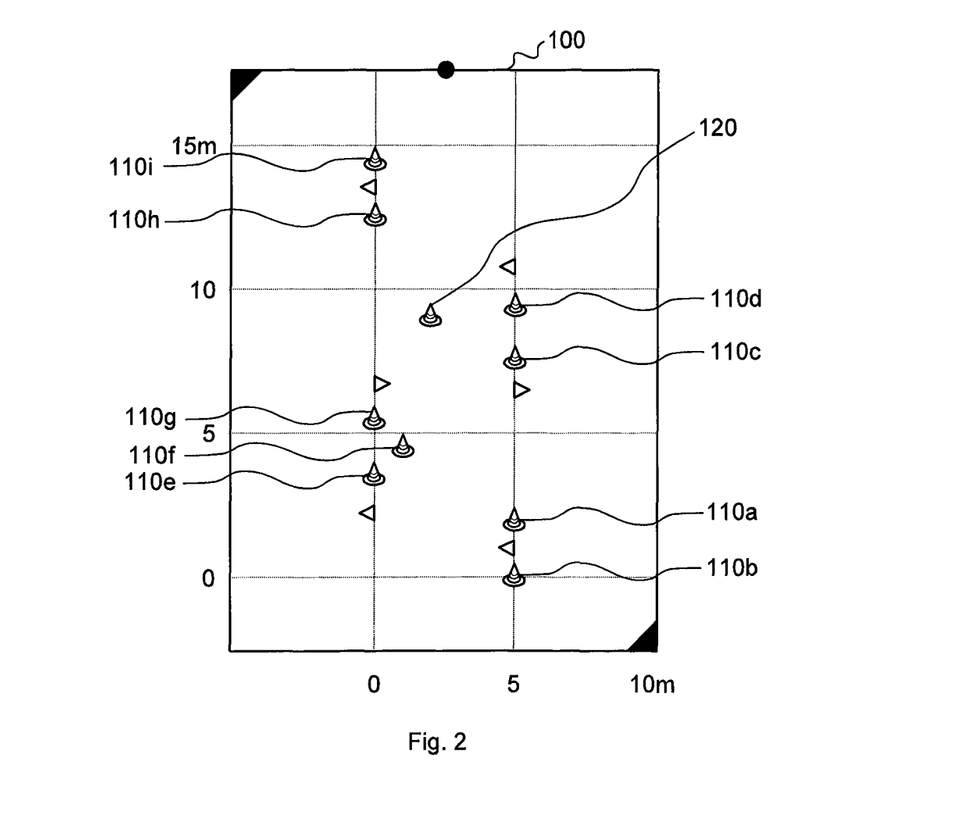
FIG. 2 shows an example for a graphical representation of an exercise area and of the objects involved in the training exercise.

FIG. 2 shows a graphical representation of an exercise set-up within an exercise area 100. Exercise objects 110a to 110j within the exercise area 100 serve as an example for one of many possibilities as to how exercise objects may be provided and/or visualized. Several exercise objects 110a-110j are shown here in FIG. 2 within the bordered predetermined exercise area 100 illustrated. Cones or polygons are stated here merely as an example for exercise objects 100 around which the athletes should run during a training exercise and which correspond to real objects. FIG. 2 also shows the determination logic, e.g., an implied light barrier between objects 110h and 100i and/or objects 110a and 110b comprising a trigger in direction of arrow. Further, at 110c, 110d, 110e and 110g, light barriers are unilaterally tied to the cones, i.e., they move together with the positions of the real cones, but do not change their relative position thereto. In this respect, light barrier (110a→110b) is defined as the start light barrier, light barrier (110h→110i) is defined as the end light barrier. All further light barriers serve as intermediate-time timers which might be defined in any order.

For example, the exercise template may initially only be prepared in a virtual form, i.e., may be created using a graphical user interface. Alternatively or supplementary, the materials and/or the exercise objects used in the exercise may be placed and/or set up simultaneously on a real exercise area as well which corresponds to the graphical illustration of FIG. 2. For this purpose, exercise objects may be set up at the virtually predetermined positions or exercise objects may be set up on the real exercise area of which the position is then incorporated into the graphical representation of FIG. 2 using a position sensing system. This may also be referred to as automatic "snapping" of tracked real material and/or of exercise objects.

An alternative already mentioned is preparing the exercise and/or drawing up the template of an exercise without any real material being present within a pitch and/or the exercise area 100. The untracked material and/or the immovable objects may then in addition be shifted and/or finely adjusted both in the graphical user interface and in a real setting. For example, this may be done by shifting a prepared template of a training exercise until the same coincides with the objects determined by the real exercise objects, whereby the template locks into place on the real positions. To simplify, the template may here be scaled or an automatic or manual translation of individual objects may be performed to, partly in an automated manner, compensate for deviations of the template from the real set-up. For the same purpose, parts of or the entire template may possibly be rotated as well.

If several movable objects and/or athletes participate in the exercise, several athletes may be associated with different teams. This may be done either manually by clicking on and/or marking individual movable objects and putting them together to teams or by simultaneously marking several movable objects which are thus labelled as belonging to one team. A possible alternative is the automatic association with teams, such as by means of the initial line-up of the athletes and/or of the movable objects, by means of the passing through specific goals, whether real or virtual, or by setting up the movable objects and/or the individual athletes at specific markers or in specific boxes.

While the previous considerations related to the method for automatically evaluating a progression of a training exercise, a brief summary is given in the following paragraphs as to how the prerequisites may be created for the training exercise to be held in a real setting on a training ground and/or within a predetermined exercise area. First, the immovable objects previously defined may be arranged within the exercise area. For this purpose, acoustic or visual feedbacks may be given for the correct placing of tracked training material, i.e., of such objects of which the positions may also be determined using an automatic position sensing system. This may, for example, be supported by an acoustic feedback in which the frequency of a beeping becomes faster the closer the immovable object to be placed is to its desired position. For example, the desired position may be indicated with the help of a continuous tone. Another possibility would be an announcement by a computer-aided speech synthesis. Alternatively, the set-up of the real exercise may be supported by other measures, such as by projecting the desired positions within the real exercise area, e.g., using a beamer, a video floor or by laser markings.

Providing the location information for the tracked movable objects may be done by recording the positions at successive points in time. For this purpose, the exercise may, for example, be started manually, i.e., the start of the recording may be triggered manually. Alternatively, the exercise may also be started in an automated manner by, for example, a pre-configured event being observed by at least one movable object. For example, this may be the crossing of a virtual line by a movable object and/or a player within the exercise area. The connecting line between the objects

110a and 110b in FIG. 2 may be considered to be an example for such a virtual line. Crossing through this virtual light barrier may, for example, start a recording of location information or indicate the start of a training exercise.

After termination of the real exercise, determining or recording the plurality of location information for the movable objects and/or athletes or players participating in the training exercise is completed so that these pieces of information may be fed, and/or may be passed on, to the method for automatically evaluating the training exercise. Alternatively, the evaluation may be done without recording if the location information is passed on to the method for automatic evaluation in real time. In this case, only the evaluation results are stored for later displays.

By comparing the position information and the exercise targets, the progression of the training exercise is then determined. For example, circuits (Durchläufe) of athletes and/or the number of rounds which an athlete has completed within an exercise course may be determined here, without this claiming to be exhaustive. Further, times, distances and similar may be determined. Specific events and/or their occurrence may also be an indication for the evaluation of a training exercise, e.g., achieving of specific split times/intermediate times or complying with predetermined lap times and/or distances covered per time unit as well as complying with predetermined distances to training materials or similar.

After evaluating the progression of the training exercise, either the evaluation as such may be stored in the database for further use and analysis or the exercise targets as well as the recorded and/or provided location information may be filed in a database or in a storage system to be able to repeatedly perform an evaluation of the progression of the training exercise at a later point in time.

Just as the beginning of a real exercise, the ending of a real training exercise may also be performed manually and/or in an automated manner, e.g., if a predetermined and or pre-configured event occurs. For example, this may be the leaving of the exercise area 100 by a movable object and/or by a player or the crossing of a further virtual light barrier, e.g., between the objects 110h and 110i.

Figure 3:
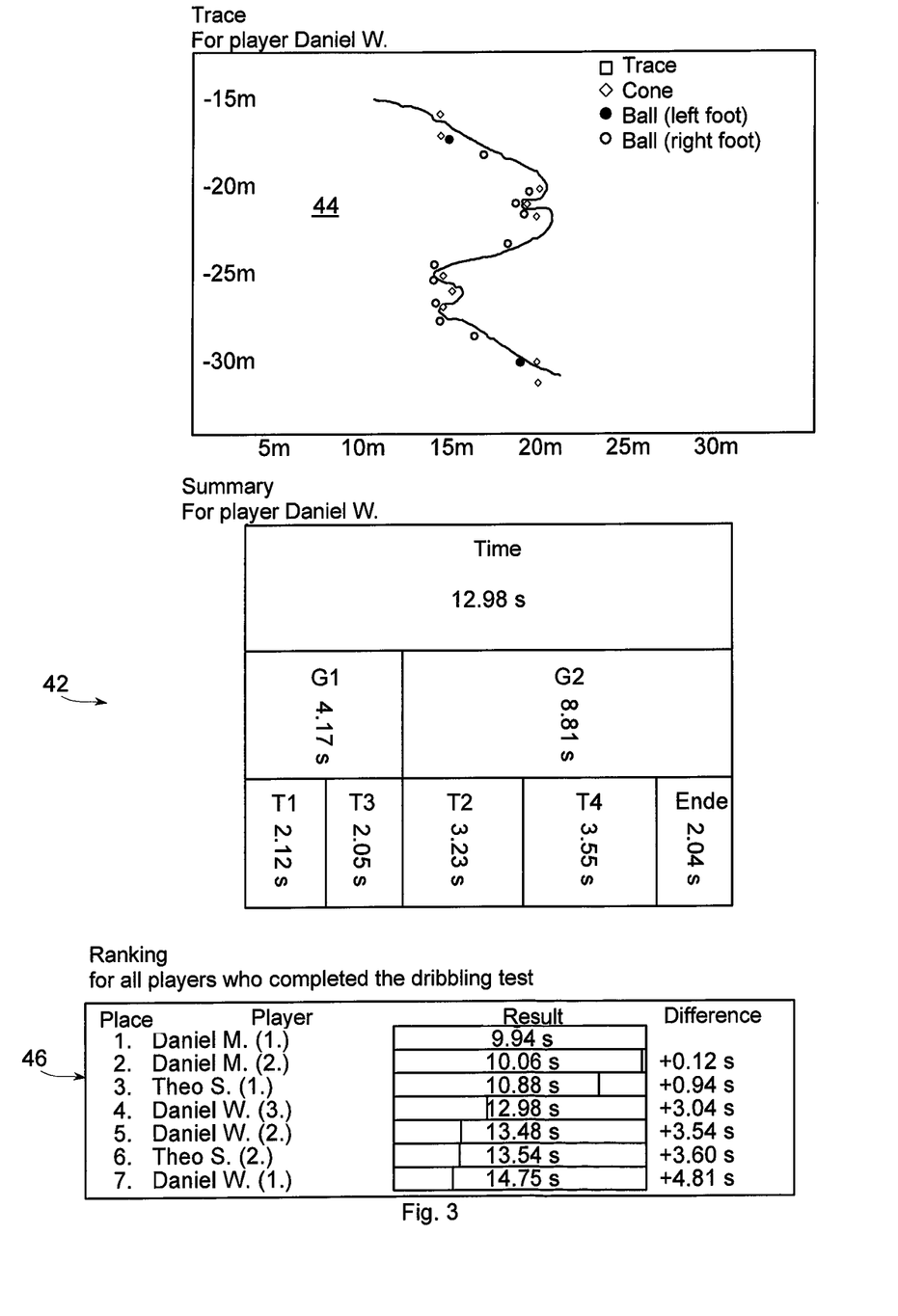
FIG. 3 shows an example for a graphical display representing the evaluation of the progression of the training exercise.

According to some embodiments, the result of the evaluation is also illustrated and/or visualized in a graphic. FIG. 3 shows a schematic view of a possible visualization of the analysis and/or the evaluation of the training exercise.

As an example for a possible visualization, FIG. 3 shows—in the illustration in the middle 42—several intermediate times achieved and the end time achieved of a soccer player's dribbling visualized in the illustration in the middle in tabular form. The upper illustration 44 shows a trajectory 115 of the soccer ball 20 as a movable object 120, i.e., the temporal progression of the position of the movable object 120 relative to the position of a plurality of further exercise objects 110a-110i. In the example illustrated in FIG. 3, the plurality of location information is tracked and/or provided for a soccer ball 120 as a movable object. As a further movable object, in further embodiments, the position of a player dribbling with the ball might additionally be tracked as an example. In the bottom illustration 46, the end times of a plurality of participants taking part in the training exercise are compared relative to one another in the form of a tabular illustration to visually give a feedback as to which one of the participants has completed the training exercise with the best performance.

Further forms of visualization not illustrated for reasons of clarity may, for example, be the illustration in tabular form, the illustration of graphs, heat maps, traces or similar.

Furthermore, according to further embodiments, cross-sectional comparisons between different athletes or longitudinal comparisons between several circuits of an exercise of the same athlete may, for example, be illustrated in graphical form. Furthermore, longitudinal comparisons between several circuits completed by an athlete may, for example, be illustrated across several implementations of the same exercise template.

According to some embodiments, the data may be exported as already described above. This may enable the training exercise to be supplemented with further determination logics and/or exercise targets which were previously not configured.

Storing the results and/or the evaluation in a database may be done either while the analysis and/or the evaluation of the success is ongoing or after the same has been completed. As stated in the preceding paragraphs, the order is not specified in the implementation of the steps of the method for automatically evaluating a success of a progression of a training exercise. For example, according to some embodiments, first the location information may also be provided and/or the positions may be recorded, before an exercise template is drawn up or the exercise targets are defined. First, an exercise may virtually be performed and recorded without a defined target, whereupon the definition is subsequently made as to how the evaluation of the success of the implementation of the exercise should be carried out.

The individual components and/or partial aspects of an embodiment of a method for automatically evaluating a success of a progression of a training exercise are again summarized in other words below.

In an editor unit, a user may draw up exercise templates. For the exercise template, the area of an exercise and the material used are set. If necessary, material may be pre-placed. All placements are here relative to the exercise area. The exercise area may be shifted to any absolute position accessible to a tracking unit and/or a position tracking system. Furthermore, the user sets the determination logic, i.e., they determine what should be analyzed in the exercise. This may, for example, be the setting of light barriers and the order of running through them. Light barriers may also be executed as "virtual light barriers". In this respect, a "virtual light barrier" comprises a connection of two coordinates which, when overstepping (a tag and/or a person with a tag) in a specific direction or in both directions may trigger an event in the analyzer. The coordinates may here also be tied to material and/or immovable objects to tie, e.g., light barriers between two cones or light barriers between a cone and a coordinate relative to the same or an absolute coordinate to the real position of a tracked object. Further, analyses may be carried out, such as the analysis of ball contacts, changes of athlete or a movement of a specific material (e.g., pass between two players in soccer, handing over the baton in a relay race).

The exercise template determined in this way is placed on an exercise area. At this point in time, the tracking unit and/or a position determining system may already supply tracking data with the help of which the exercise may be placed and/or set up automatically and/or semi-automatically (by placing the user and automatic "locking in place" on tracked material/lines/etc.). In this context, real entities of tracked objects are associated with the objects set in the editor.

A placed exercise is then started either by user interaction or automatically by an event set in the editor. That means, the exercise is switched to active. This may be done automatically, e.g., by overstepping a light barrier defined as the start. An exercise may also be started without using a template. If the tracking data is recorded in this context, exercise templates may be drawn up, placed and analyzed afterwards.

While an exercise is active, relevant events may already be analyzed, stored and illustrated. This may be, e.g., lap times, ball contacts, any overstepping of light barriers or lines, recognizing passes or similar. These results may be visualized for the user.

Like the start, the end of an exercise may be signalized by a manual stop on the part of the user or by an event set in the exercise template.

During the exercise or upon completion of an exercise, the events may be visualized within the exercise. This may be done using tables, graphs, heat maps, traces or other visualizations. By way of interactivity, the user may select individual athletes and results within an exercise and may compare them with each other (cross-sectional analysis). Thus, e.g., rankings of circuits completed or sorting by specific events (e.g., maximum/minimum distance) is possible. It is also possible to visualize the longitudinal section of specific athletes, i.e., to analyze and to visualize the results of an athlete for an exercise template of several implementations (within an exercise or exercises carried out in the past). In addition, the user has the option to add further new analyses. If necessary, the analyzer unit needs to reanalyze the exercise. By selecting an event and/or event period in the (filtered) list of events within an exercise, the user may arrive at the relevant point in time in a replay and/or a repeat playback of the exercise using a graphical representation of the exercise, as it is for example shown in FIG. 2. It is also possible to link the replay/event with real video data, i.e., with the playback of a video recording of the implementation of the exercise.

All results of an exercise may already be stored during the implementation of the exercise or after deactivating the exercise. The data may be used, e.g. for longitudinal visualizations.

FIG. 4 shows again a schematic view of an embodiment of an analyzer 50 for evaluating the progression of a training exercise. The analyzer 50 comprises an input interface 52. The same is configured to provide, or, as an alternative, to receive from an external source, a plurality of location information for at least one movable object participating in the training exercise. A storage 54 is configured to provide at least one predetermined exercise target. A comparator 56 connected to the input interface 52 and the storage 54 is configured to compare the plurality of location information with the exercise target, and to transmit the result of the comparison to an evaluator 58. The evaluator 58 again is configured to evaluate the progression of the training exercise based on the result of the comparison and to make the evaluation available to a user of the system and/or of the analyzer according to one of the options described above.

Figure 4:
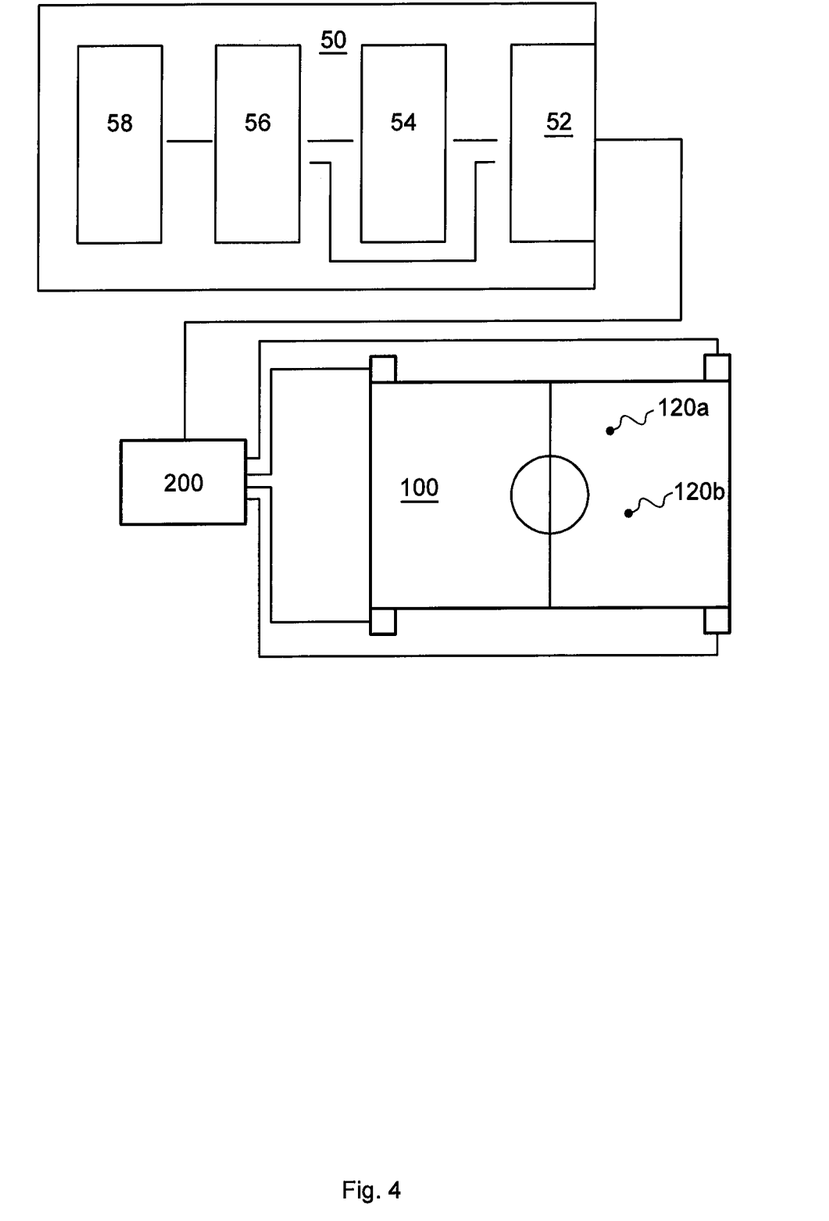
FIG. 4 shows a schematic illustration of an embodiment of an analyzer for evaluating a progression of a training exercise.

As schematically illustrated in FIG. 4, the analyzer 50 may optionally be part of a system for evaluating a progression of a training exercise, further comprising a position sensing system 200 configured to sense location information for at least one movable object participating in the training exercise within the exercise area 100. For this purpose, the position sensing system 200 may, for example, dispose of a plurality of radio receivers or transmitters 220a-220d by means of which the position of movable objects 120a or 120b within the exercise area 100 may be determined and/or tracked. In FIG. 4, a soccer pitch is indicated as the exercise area 100 as an example only on which the position of two players 120a and 120b is determined by the position sensing system 200. In further embodiments, only parts of the pitch may be used as an exercise ground as well. The position sensing system 200 may also store the location information about the time of at least one object participating in the training exercise within the exercise area 100 and, if necessary, replay it at a later point in time.

Even though the above description mainly illustrates applications, wherein a plurality of athletes interact, e.g., in soccer exercises and/or training exercises for soccer players, further embodiments of the present invention may also be used in other areas of application in sport. For example, further embodiments may be used for performance diagnostics of any top-level competitive sports in which also only one athlete may be involved, e.g., in all athletic disciplines. For evaluating a training exercise, not only, for example, an absolute position of an athlete and/or a movable object in space may be determined, but several positions may be determined or used for or at a single athlete for this purpose to determine the success of a training exercise. For example, several tags and/or position sensing sensors may be attached to athletes' limbs so that, in addition to a position of an athlete's center of gravity, further information with regard to their body posture may also be taken into account to evaluate the success of a training exercise. For example, this may be used to observe the technique of high jumpers, pole vaulters or of athletes of other athletic disciplines, and to decide in connection with suitable exercise targets as to whether or not the same has performed the motion sequences typical for their sport with sufficient precision during the training exercise.

The features disclosed in the previous description, the following claims and the enclosed figures may either individually or in any combination be of importance or implemented for the realization of an embodiment in their different designs.

Even though some aspects were described in connection with a device, it is understood that those aspects also represent a description of the corresponding method so that a block or a component of a device shall also be understood to be a corresponding method step or a feature of a method step. In line with that, aspects described in connection with a, or as a, method step also represent a description of a corresponding block or detail or feature of a corresponding device.

Depending on specific implementation requirements, embodiments of the invention may be implemented in hardware or in software. The implementation may be performed using a digital storage medium, such as a floppy disk, a DVD, a Blu-ray disc, a CD, a ROM, a PROM, an EPROM, an EEPROM or a FLASH memory, a hard drive or any other magnetic or optical storage on which electronically readable control signals are stored which are capable of interacting or do interact with a programmable hardware component such that the respective method is executed.

A programmable hardware component may be formed by a processor, a computer processor (CPU=Central Processing Unit), a graphics processor (GPU=Graphical Processing Unit), a computer, a computer system, an application-specific integrated circuit (ASIC), an integrated circuit (IC), a system on chip (SOC=System on Chip), a programmable logic element or a field programmable gate array (FPGA) with a microprocessor.

The digital storage medium may therefore be machine or computer-readable. Thus, some embodiments comprise a data carrier which comprises electronically readable control signals which are capable of interacting with a programmable computer system or a programmable hardware component in a way that one of the methods described herein is executed. Thus, an embodiment is a data carrier (or a digital storage medium or a computer-readable medium) on which the program for executing one of the methods described herein is recorded.

In general, embodiments of the present invention may be implemented as a program, firmware, a computer program or a computer program product with a program code or as data, wherein the program code or the data is operable to execute one of the methods if the program runs on a processor or a programmable hardware component. For example, the program or the data may also be stored on a machine readable carrier or data carrier. The program code or the data may be available as a source code, a machine code or a byte code, amongst others, and as another intermediate code.

Moreover, a further embodiment is a data stream, a signal string or a sequence of signals which represent the program for executing one of the methods described herein. The data stream, the signal string or the sequence of signals may, for example, be configured to be transferred via a data communication connection, e.g. via the Internet or another network. Thus, embodiments are also data-representing signal strings suitable for transmission via a network or a data communication connection, wherein the data represents the program.

A program according to an embodiment may execute one of the methods during its execution, for example, by the same reading out memory locations or by writing a datum or several data into the memory locations, whereby switching operations or other operations are possibly caused in transistor structures, in amplifier structures or in other electrical, optical, magnetic members, or members which operate according to another functional principle. Accordingly, data, values, sensor values or other information can be sensed, determined or measured by a program, by reading out a memory location. Therefore, a program can sense, determine or measure sizes, values, measured quantities and other information by reading out one or several memory locations, and may cause, arrange for or execute an action by writing into one or several memory locations, as well as control other equipment, machines and components.

The embodiments described above merely illustrate the principles of the present invention. It will be understood that modifications and variations of the arrangements and details described herein are clear to other persons skilled in the art. Therefore, it is intended that the invention be merely limited by the scope of the following patent claims and not by the specific details which were presented on the basis of the description and the explanation of the embodiments.

The invention claimed is:

1. A method for automatically evaluating a progression of a training exercise of a participant, comprising:
    providing location information for at least one movable object participating in the training exercise of the participant, wherein the at least one movable object includes an item whose location is separate and independent from a location of any participant of the training exercise and used during the training exercise of the participant;
    providing at least one predetermined exercise target;
    providing further-location information using a graphical user interface which comprises a graphical representation of an exercise area and a graphical representation of an exercise object in a graphical display, wherein the further location information indicates a position of the exercise object involved in the training exercise within the exercise area or a time-invariant position within the exercise area corresponding to a predetermined progression of the training exercise;
    comparing the location information of the at least one movable object or a quantity derived from the location information of the at least one movable object to the exercise target; and
    evaluating the progression of the training exercise based on the result of the comparison, wherein providing the at least one predetermined exercise target comprises selecting at least one used determination logic for the location information from a plurality of available determination logics.

2. The method of claim 1, wherein, according to the determination logic used, based on the location information a tactical parameter or a technical parameter is determined for a type of sport.

3. The method of claim 1, wherein, according to the determination logic used, based on the location information an athletic parameter is determined for at least one person involved in the training exercise.

4. The method of claim 1, wherein a piece of location information for an object in each case indicates a position of the object within a predetermined exercise area.

5. The method of claim 4, wherein the position is indicated by coordinates of the object in any coordinate system associated with the training exercise.

6. The method of claim 5, wherein providing the location information for the at least one movable object comprises determining the position of the movable object within the exercise area using a position tracking system at several successive points in time.

7. The method of claim 1, wherein providing the further location information comprises a user input of the position.

8. The method of claim 1, wherein providing the further location information comprises determining the position of the exercise object in the exercise area using a position tracking system.

9. The method of claim 8, wherein providing the further location information comprises moving the graphical representation of the exercise object on the graphical display.

10. The method of claim 1, wherein providing the further location information comprises comparing the position of the graphical representation of the exercise object within the graphical representation of the exercise area to the position of the exercise object determined using a position tracking system within the exercise area.

11. The method of claim 10, wherein the graphical representation of the exercise object is changed on the graphical display starting from a predefined initial position such that the position of the graphical representation of the exercise object within the graphical representation of the exercise area corresponds to the position of the exercise object determined using the position tracking system within the exercise area.

12. The method of claim 11, wherein the graphical representation of the exercise object is changed by shifting the graphical representation of the exercise object relative to the graphical representation of the exercise area, a rotation of the graphical display or a scaling of the graphical display.

13. The method of claim 12, wherein an initial graphical representation of the exercise object involved in the training exercise in the exercise area is changed such that the position of the graphical representation of the exercise object within the graphical representation of the exercise area corresponds to a position of the exercise object determined using the position tracking system within the exercise area, wherein the initial graphical representation is automatically changed by shifting the graphical representation of the exercise object relative to the graphical representation of the exercise area, a rotation of the graphical display or a scaling of the graphical display.

14. The method of claim 10, wherein a position of the exercise object within the exercise area is changed such that the position of the exercise object determined using the position tracking system within the exercise area corresponds to the position of the graphical representation of the exercise object within the graphical representation of the exercise area.

15. The method of claim 14, further comprising:
providing an acoustic, visual or haptic signal by the position tracking system which comprises a piece of information about a deviation between the position of the exercise object within the exercise area and the position of the graphical representation of the exercise object within the graphical representation of the exercise area.

16. The method of claim 1, wherein providing the at least one predetermined exercise target comprises defining parameters which are determined for the movable object based on the location information to evaluate the progression of the training exercise.

17. The method of claim 1, wherein the exercise target is at least one of entering of the movable object into a predetermined sector within the exercise area, interacting of the movable object with a further object, reaching of a predetermined speed by the movable object and the location information being consistent with a predetermined sequence of location information.

18. The method of claim 1, wherein providing the exercise target comprises defining all movable objects and all exercise objects involved in the training exercise.

19. The method of claim 15, wherein providing the exercise target comprises defining a desired interaction between the movable object and at least one further exercise object involved in the training exercise.

20. The method of claim 1, further comprising:
storing the location information and the exercise target.

21. The method of claim 1, wherein evaluating the progression of the training exercise comprises displaying a visual illustration of the results of the comparison on a display.

22. An analyzer for evaluating a progression of a training exercise of a participant, comprising:
an input interface configured to provide location information for at least one movable object participating in the training exercise of the participant, wherein the at least one movable object includes an item whose location is separate and independent from a location of any participant of the training exercise and used during the training exercise of the participant;
a storage configured to provide at least one predetermined exercise target;
a graphical user interface which comprises a graphical representation of an exercise area and a graphical representation of an exercise object corresponding to further location information in a graphical display, and by means of which the further location information is provided, wherein the further location information indicates a position of the exercise object involved in the training exercise within the exercise area or a time-invariant position within the exercise area corresponding to a predetermined progression of the training exercise;
a comparator configured to compare the location information of the at least one movable object or a quantity derived from the location information of the at least one movable object to the at least one predetermined exercise target associated with the training exercise, and
an evaluator configured to evaluate the progression of the training exercise based on a result of the comparison.

23. A system for evaluating a progression of a training exercise of a participant, comprising:
a position sensing system configured to sense location information for at least one movable object participating in the training exercise of the participant within an exercise area, wherein the at least one movable object includes an item whose location is separate and independent from a location of any participant of the training exercise and used during the training exercise of the participant; and
an analyzer for evaluating the progression of the training exercise, the analyzer comprising:
an input interface configured to provide location information for the at least one movable object participating in the training exercise;
a storage configured to provide at least one predetermined exercise target;
a graphical user interface which comprises a graphical representation of an exercise area and a graphical representation of an exercise object corresponding to further location information in a graphical display, and by means of which the further location information is provided, wherein the further location information indicates a position of the exercise object involved in the training exercise within the exercise area or a time-invariant position within the exercise area corresponding to a predetermined progression of the training exercise;
a comparator configured to compare the location information of the at least one movable object or a quantity derived from the location information of the at least one movable object to the at least one predetermined exercise target associated with the training exercise, and
an evaluator configured to evaluate the progression of the training exercise based on a result of the comparison.

* * * * *